(12) United States Patent
Abdel-Rahman et al.

(10) Patent No.: US 6,448,777 B1
(45) Date of Patent: Sep. 10, 2002

(54) HERMETICALLY-SEALED MINIATURIZED DISCHARGE IONIZATION DETECTOR

(75) Inventors: Mahmoud F. Abdel-Rahman, Newark; Andrew M. Warchol, Wilmington, both of DE (US); James W. Baker, Elkton, MD (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/931,927

(22) Filed: Aug. 20, 2001

(51) Int. Cl.[7] .............................................. G01N 27/62
(52) U.S. Cl. ....................................................... 324/464
(58) Field of Search ................................. 324/464, 468, 324/465, 466, 459; 250/288, 382

(56) References Cited

U.S. PATENT DOCUMENTS 6,107,805 A * 8/2000 Abdel-Rahman ........... 324/464

* cited by examiner

Primary Examiner—N. Le
Assistant Examiner—James Kerveros

(57) ABSTRACT

An apparatus for and method of making a discharge ionization detector. The apparatus comprises a detector body, a detector cavity, located in the detector body and having a discharge electrode and an second discharge electrode, wherein an electric discharge runs between the second discharge electrode and the discharge electrode, and a signal electrode which attracts ionized molecules, an inlet interface, through which a discharge gas enters the detector, an analyte inlet, through which the analyte enters the detector cavity, and an outlet through which the analyte and discharge gas exit the detector body, wherein the apparatus is hermetically sealed. The apparatus is hermetically sealed by vacuum brazing the components to the detector body. The present invention can also have a detector volume as small as 10 micro-liters or less. The method comprises machining a body material to form a detector body, by forming a detector cavity, a column bore and a plurality of electrode bores, preparing the body surface for bonding, and bonding a plurality of electrodes, an inlet interface, a column interface and a vent interface to the detector body, whereby a hermetically sealed system is formed that has a detection zone volume of approximately 5–100 micro-liters.

26 Claims, 4 Drawing Sheets

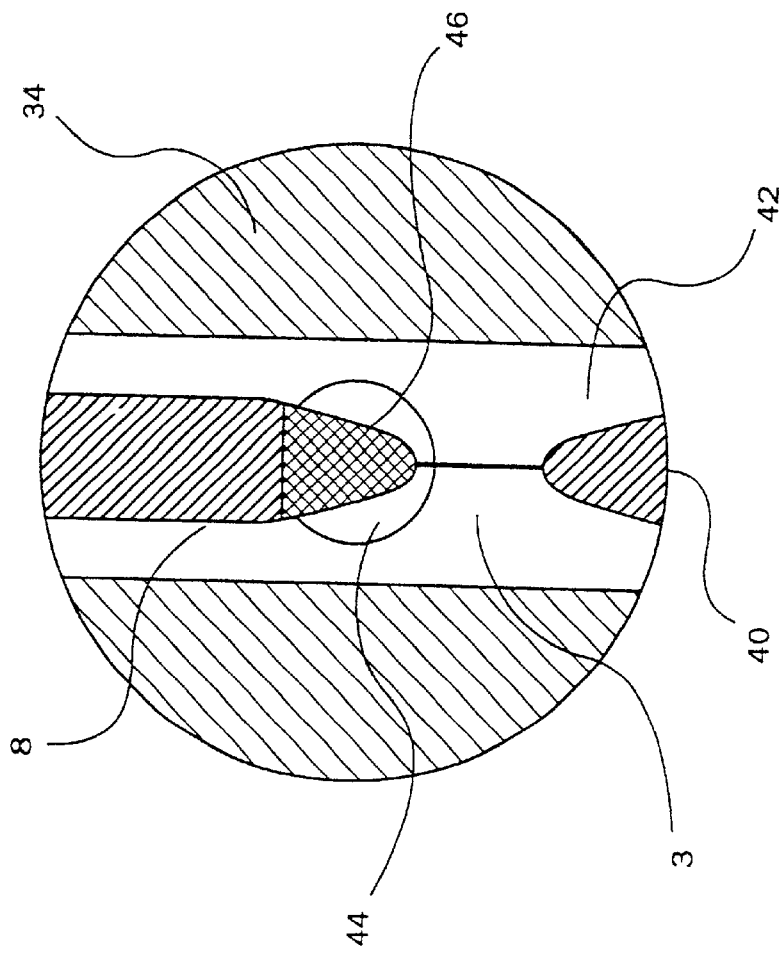

HERMETICALLY-SEALED MINIATURIZED DISCHARGE IONIZATION DETECTOR

CROSS-REFERENCE TO RELATED APPLICATION(S)

None.

FIELD OF THE INVENTION

The present invention relates to ionization detector devices. More specifically, the present invention relates to an apparatus and a method of making a hermetically sealed discharge ionization detector having a small detection volume.

BACKGROUND OF THE INVENTION

As illustrated in FIG. 1, an ionization detector 100 typically comprises a body 102 having a first chamber 110 for generation of ionizing particles and a second chamber 120 connected to the first chamber 110 for receiving a sample gas 122. The sample gas 122 is conveyed in a carrier gas and is provided to the second chamber 120 by a conduit 130 which typically is provided in the form of a separation column. The first chamber 110 includes a source of ionizing particles (not shown), such as a radioactive source or an electrical discharge, and is typically swept by a detector or carrier gas 112 selected from the class of known noble gases. The presence of the detector gas 112 in the first chamber 110 causes ionizing particles, in the form of photons and metastables, to be produced. The flow of the detector gas 112 from the first chamber 110 to the second chamber 120 causes the ionized particles to be mixed with the sample gas 122, thus causing the sample molecules of interest, considered herein as analytes, to be ionized. The second chamber 120 includes electrodes 124, 126, 128 for detecting the ionized sample molecules by use of an electrometer circuit (not shown) connected to the electrodes 124, 126, 128.

Detector sensitivity may be measured in a plot of detector response versus analyte concentration or analyte quantity. The range over which the detector sensitivity is constant is called the linear dynamic range, and the entire range over which the response is variable with analyte concentration or quantity is called the dynamic range of the detector. The upper limit of the dynamic range is determined when detector sensitivity falls to an unusable value, typically zero, and the detector is said to be saturated. The lower limit of the dynamic range occurs at a minimum detectable level (MDL).

A discharge ionization detector is an ultra sensitive detector used in gas chromatography. A discharge ionization detector operates by applying a high voltage across discharge electrodes that are located in a gas-filled source chamber. In the presence of a detector gas such as helium, a characteristic discharge emission of photons occurs. The photons irradiate an ionization chamber receiving a sample gas that contains an analyte of interest. Ions are produced in the ionization chamber as a result of photon interaction with ionizable molecules in the sample gas. Helium metastables are also generated in the source chamber and are found to play a role in ionization of the analyte of interest.

A discharge ionization detector can run in a universal, selective, or electron capture mode.

An electrical discharge arc excites the detector gas to glow and give off high energy photons, and excite the detector gas atoms to a metastable level. If the energy of an incoming photon is high enough, photo-excitation can occur to such an extent that an electron is completely removed from its molecular orbital. This is called photo-ionization. A typical photo-ionization reaction resembles the following:

$$R + h\nu \rightarrow R^+ + e^-$$

Also, the metastable atoms can transfer their energy to other molecules during tertiary collisions. If the ionization potential of the analyte molecules is lower than the energy of the photon or the metastable atom, the bombarded or colliding molecule is ionized.

If helium is used as the detector gas, the detector will detect all gases other than helium, because helium has a higher ionization potential than all other gases. This is called the universal mode of detection. UV photon emissions and excited helium atoms in the electrical discharge acquire such energies sufficient to ionize all other gases. When a sample analyte elutes from the chromatographic column into the detector, it becomes partially ionized. The ionized analyte molecules are collected and measured. The electrical current measurement is representative of the analyte presence in the detector. The detector body is usually heated to prevent high boiling sample analytes from depositing on the detector internal surfaces.

Other noble gases with lower ionization potential can be used instead of helium. In this case only sample analytes having lower ionization potential than the noble gas used can be ionized and detected. Thus the detector becomes selective according to analyte ionization potential. This is the selective mode of operation. This can be extremely useful for differentiating between compounds that have similar boiling points but different ionization potentials.

When methane is added to the sample flow, it is ionized by the helium discharge, producing thermal electrons. Any electron-capturing analyte present can capture these thermal electrons and the detector, with some adaptation, can function as an Electron Capture Detector. This is the electron capture mode of operation.

Electron capture detectors for gas chromatography are well known in the art. This type of detector offers high sensitivity and high selectivity towards electrophilic compounds and is widely used for detecting trace amounts of pesticides in biological systems and in food products. Such compounds typically contain halogens which combine with free electrons that are created in the ionization chamber in the detector. The resulting decrease in free electrons in the ionization cell is monitored as an indication of the concentration of the compounds in a sample.

Certain improvements and modifications have been made to ionization detectors in order to overcome certain problems inherent in the prior art. For instance, a funnel-shaped detector cavity, designed to inhibit sample analytes diffusing back towards the ionization chamber as disclosed in U.S. Pat. No. 6,037,179 to Abdel-Rahman, and an ionization detector designed to have an extended detection zone, as disclosed in U.S. Pat. No. 6,107,805 to Abdel-Rahman, both of which are incorporated herein by reference in their entirety, have alleviated or solved certain problems in the prior art, such as analyte diffusion and small linear dynamic range.

Discharge ionization detectors typically have a detector volume of approximately 150 $\mu$L. This requires large amounts of analytes, and high gas flow rates. This can be problematic, especially for ultrafast and portable gas chromatographs. Also, because of the ultra sensitivity of a discharge ionization detector, any ambient air (or other detectable gases) leaking into the detector is detected, causing the detector baseline signal to wander. This significantly increases the detector's noise and worsens the detector's MDL.

Discharge ionization detectors well known in the art, such as those made by VICI® and Gow Mac® Instrument Company, are constructed of several parts mechanically assembled together to form the final detector assembly. This type of construction uses mechanical compression of surfaces to form various seals. The seals can eventually exhibit ambient air leaks when various compressed parts expand and contract as the detector is heated and cooled. Air leaks can also develop as the various compressed parts relax over time and plastically deform. This type of construction is also difficult to miniaturize because high-precision alignment of assembled mechanical parts is extremely difficult to achieve.

What is needed is a discharge ionization detector that has a smaller detector volume and requires no or little assembly. What is also needed is a discharge ionization detector that reduces or eliminates ambient air leaks which can cause increased detector noise and loss of MDL.

BRIEF SUMMARY OF THE INVENTION

The present invention includes a discharge ionization detector consistent with any of its modes of operation including the universal, the selective and the electron-capture modes, as well as a method of making a discharge ionization detector.

The present invention overcomes the problems of high detector volume and ambient air by using a high-precision machined body that constitutes the heart of the detector. In one embodiment, the body is ceramic. Ceramic material of high purity is advantageous in order to minimize the electrical leakage current between the signal electrode and the other electrodes and metallic connectors. Because of high-precision machining, the detector cavity can be made very small. Detectors having a detection volume of about 10 $\mu$L or less can be achieved for certain embodiments. In one embodiment, a ceramic body is metallized then brazed to various electrodes and pneumatic connectors thus producing a one-piece hermetically sealed design.

A smaller detector volume allows sample analytes to be quickly swept out of the detector thus enabling the detection of narrower chromatographic peaks. A smaller detector volume enables faster chromatography, and also allows for lower gas flow rate. Lower gas consumption is highly advantageous for portable gas chromatographs.

While multiple embodiments are disclosed, still other embodiments of the present invention will become apparent to those skilled in the art from the following detailed description, wherein is shown and described only the embodiments of the invention, by way of illustration, of the best modes contemplated for carrying out the invention. As will be realized, the invention is capable of modifications in various obvious aspects, all without departing from the scope of the present invention. Accordingly, the drawings and detailed description are to be regarded as illustrative in nature and not restrictive.

BRIEF DESCRIPTION OF THE DRAWINGS

FIG. 4 is a cross-sectional view of the area of the discharge where the creation of ionizing particles takes place in the present invention as shown in FIG. 2.

DETAILED DESCRIPTION OF THE INVENTION

The present invention reduces or eliminates ambient air leaks in the discharge ionization detector, which can cause increased detector noise and wander, unreliable measurement, and loss of MDL. The result is a hermetically sealed detector. The present invention may also eliminate large detector volumes, which can be unsuitable for ultra fast GC and portable GC.

Figure 1:
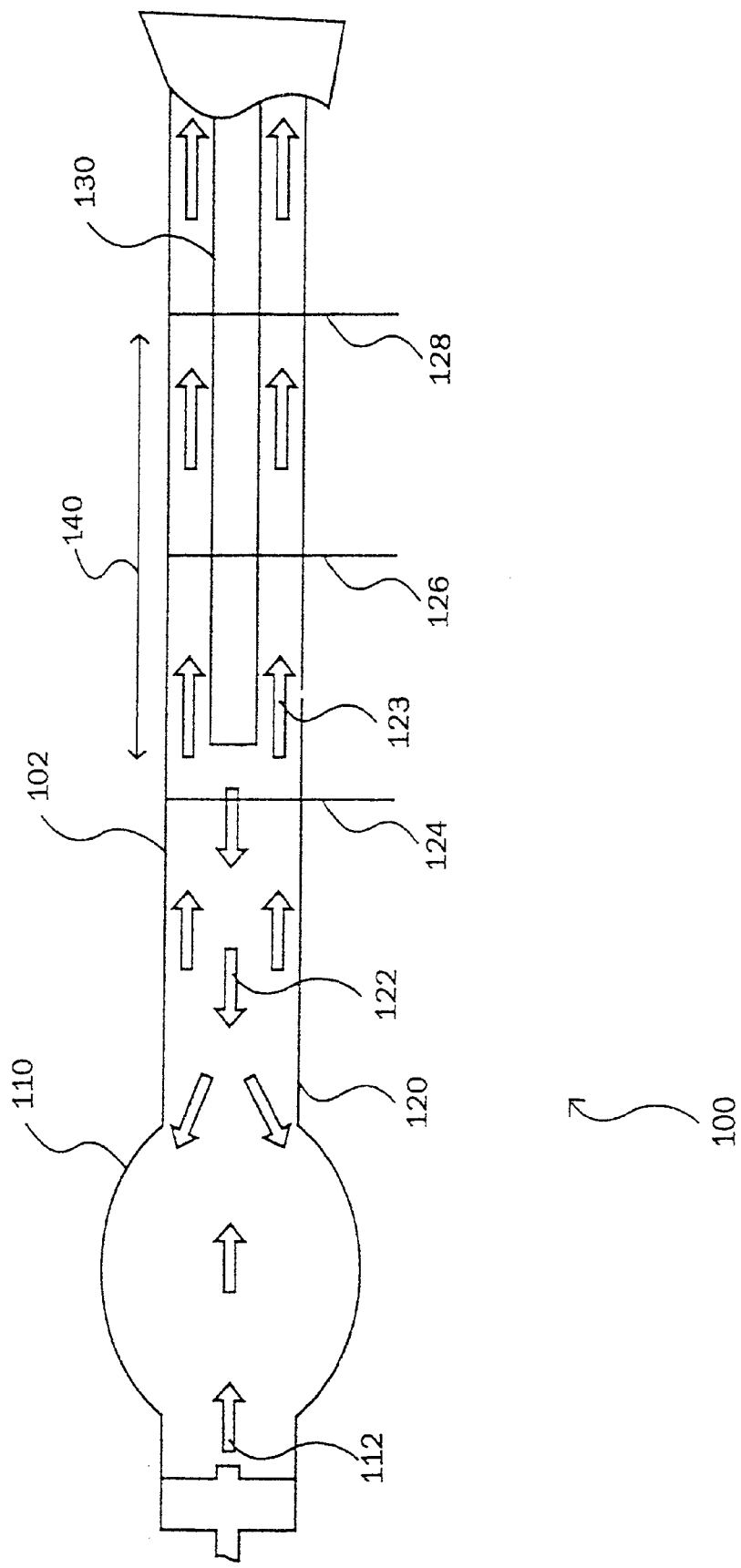
FIG. 1 is a related art ionization detector.
Figure 2:
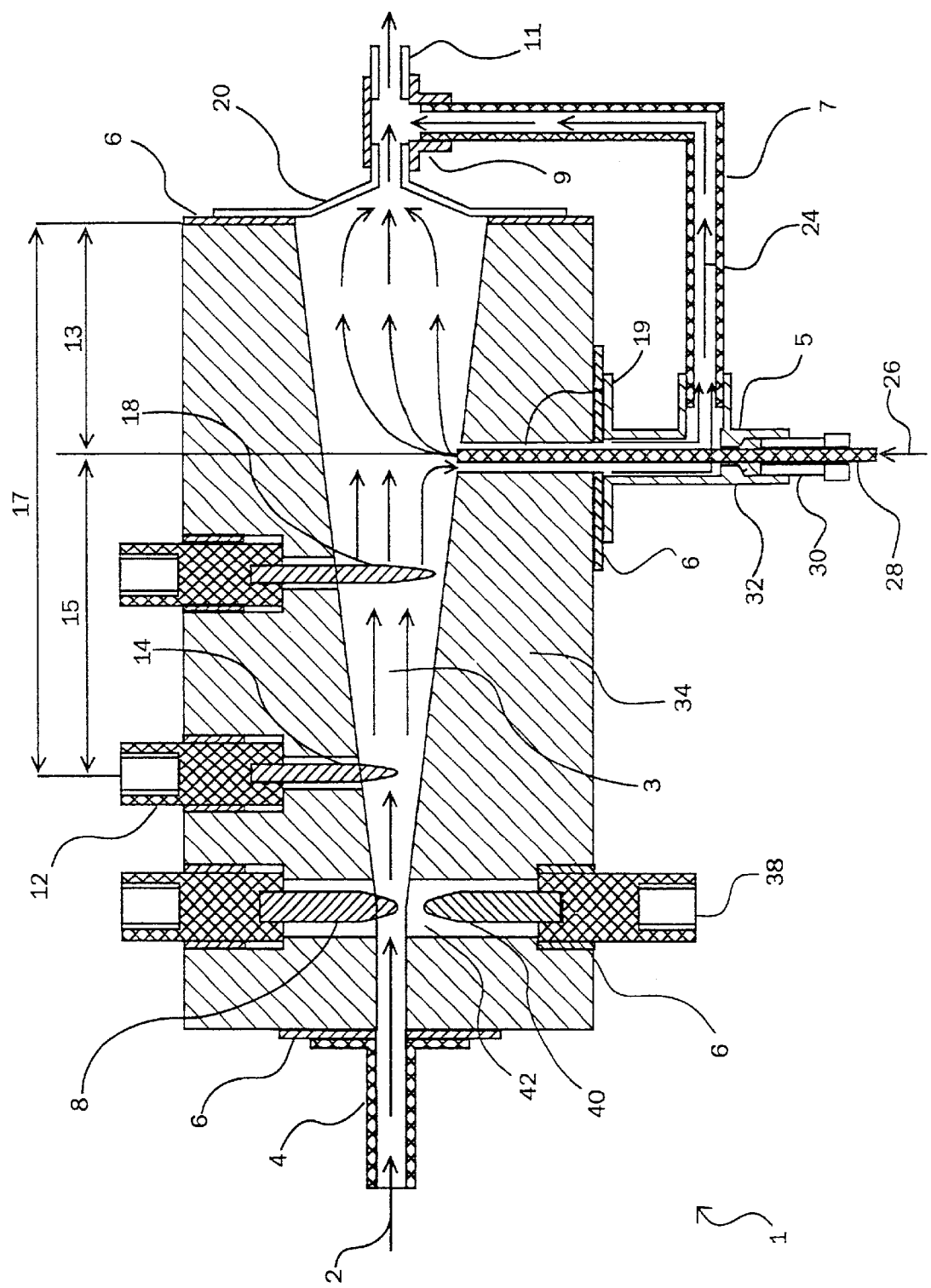
FIG. 2 is a schematic diagram of one embodiment of the present invention.

FIG. 2 shows a schematic diagram of one embodiment of the present invention. A discharge gas 2 enters the detector 1 through the inlet interface 4. The discharge gas 2 can be any noble gas. In one embodiment, the discharge gas 2 is helium. The discharge gas 2 sweeps through the detector cavity 3 passing by the discharge electrodes 8 and 40. Part of the discharge gas 2 constitutes purge gas 24 which exits the detector body through the column bore 19 and proceeds through column interface 5, purge tube 7 and finally exits through vent tube 11. This purge gas 24 keeps small air leaks developing at the column nut 30 and column ferrule 32 from disturbing the detector operation. It also prevents volatile gasses from the polymeric column ferrule 32 from entering the detector 1. The bulk of the discharge gas 2 completes its travel through the detector cavity 3 and exits through the vent interface 20 where it combines in vent tee 9 with purge flow 24 and exits through vent tube 11. In one embodiment, purge tube 7 is sized such that it allows 10%–25% of the discharge gas 2 to go through it while the remaining gas exists through vent interface 20.

Analyte 26 enters the detector cavity 3 through the chromatographic column 28. Detector cavity 3 can be funnel shaped, in the form of a conical horn as shown, to inhibit sample analytes diffusing back towards the discharge area. The electrometer or signal electrode 18 is negatively biased to collect all positive ions generated within the extended detection zone 17 which is composed of detection zone 13 and the diffusion zone 15. The guard electrode 14 and the vent interface 20 are both electrically grounded for proper establishment of the electric field. The guard electrode 14 and the vent interface 20 eliminate any potential buildup, by creating a path for the electrons freed during ionization to exit the system. The guard electrode 14 and the vent interface 20 also serve to repel positive ions away from themselves, and towards the negatively biased electrometer electrode 18.

In one embodiment, a discharge electrode 8, such as a cathode, is made of platinum or a refractory metal, such as molybdenum, to resist corrosion and sputtering. A second discharge electrode 40, such as an anode, a guard electrode 14 and signal electrode 18 can be made of similar metal for high chemical resistance. Second discharge electrode 40 and first discharge electrode 8 can form, for example, a discharge system operating according to the methodologies explained in the present specification.

In one embodiment, each electrode 8, 40, 14 and 18 is vacuum brazed to a cup-shaped holder 12. The holders 12 are made with threads 38 to allow for easy extension to the electrical connections, and are made of a metal that is easy to braze to ceramic. In one embodiment, the cup-shaped holders 12 can be made of Kovar® alloy, available from Carpenter Technology Corporation.

Kovar® alloy is a vacuum melted, Fe—Ni—Co, low expansion alloy whose chemical composition is controlled within narrow limits to assure precise uniform thermal expansion properties. Kovar® alloy is well known by those skilled in the art for making hermetic seals with ceramic materials. Kovar® is typically used in applications such as power tubes, transistors, diodes, and integrated circuits.

In one embodiment, the body 34 of the detector 1, is made of a material suitable for a hermetically sealed system. In one embodiment, the body 34 is made from ceramic. Because ceramic can withstand severe mechanical and thermal loads, and also resist abrasion and chemical attack, it is a preferable material for the body 34. In one embodiment, the ceramic material is of high electrical resistivity in order to minimize the electrical leakage current between the signal electrode and the other electrodes and metallic connectors. Because of high-precision machining, the detector cavity 3 can be made very small. Detectors having a detection volume of less than 150 $\mu$L can be achieved. Different ceramic materials that may be utilized by the present invention, include, but are not limited to alumina, silicon nitride, silicon carbide, zirconia and magnesia. And with precise machining, detection volumes of less than 100 $\mu$L, less than 50 $\mu$L, and even detection volumes of about 10 $\mu$L or less can be achieved.

Alumina is a widely used advanced ceramic material. It has very good performance in terms of wear resistance, corrosion resistance and strength at a reasonable price. In one embodiment, the alumina used is of a high purity with a low glass content. Silicon nitride has good thermal shock resistance properties. It also has low density, high strength, low thermal expansion and good corrosion resistance and fracture toughness. Silicon carbide has high corrosion resistance. It also retains its strength at temperatures as high as 1400° C. and has good wear resistance and thermal shock resistance properties. Zirconia has high strength and toughness at room temperature. The fine grain size allows for extremely smooth surfaces and sharp edges. Magnesia shares these properties and has very high electrical resistivity.

In one embodiment, the body 34 of the detector 1 is metallized in areas 6 needed for vacuum brazing. Inlet interface 4, column interface 5 and vent interface 20 are made of a metal that is easy to braze to the body 34, such as Kovar®. In one embodiment, a metallizing strip (not shown) is deposited on the surface of the ceramic body 34 to connect second discharge electrode 40 to guard 14 electrically through their respective holders 12 in order to simplify final detector assembly.

The bonded electrodes and interfaces, which seal each penetration into the cavity, in conjunction with the purge gas pathway, results in a detector system in which no unwanted gas, such as air, may enter the system and disrupt the readings, so that the system is hermetically sealed.

Figure 3:
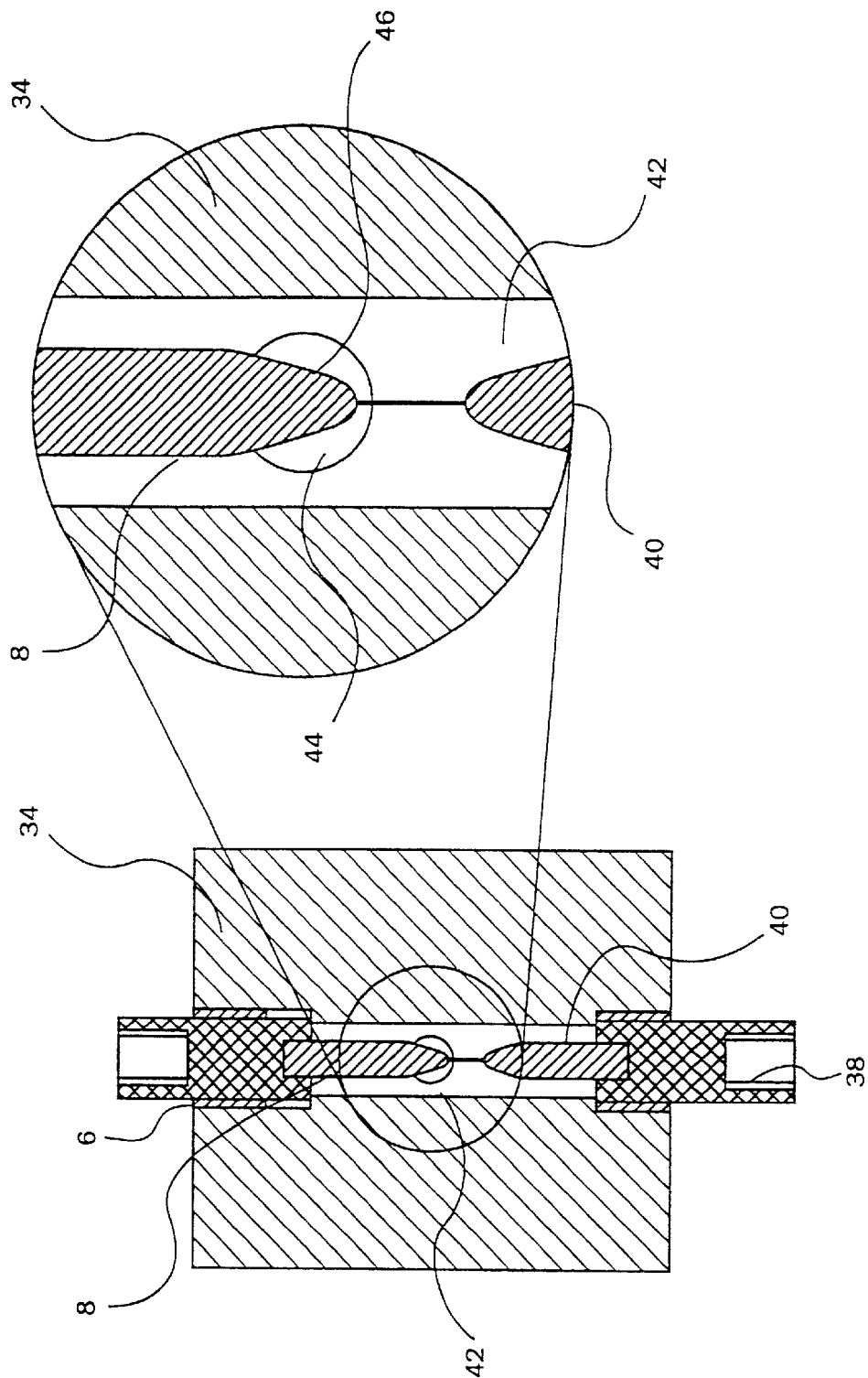
FIG. 3 is a cross-sectional view of the detector of the present invention perpendicular to the view of FIG. 2.

FIG. 3 is a cross-sectional view of the detector 1 taken at the center of the discharge electrodes 8 and 40 and perpendicular to the view of FIG. 2. A bore 42 larger than the diameter of the discharge electrodes 8 and 40 allows for sufficient spacing between the gas discharge and the ceramic walls without enlarging the detector cavity cross-sectional area 44. In one embodiment, this cross section area 44 is kept small to increase gas linear velocity and inhibit sample back diffusion.

FIG. 4 shows the areas of the discharge 46 where ionizing particles, such as UV photons and metastable atoms are created at the tip of the discharge electrode 8. Maximizing the projection of that area into the detection cavity 3 helps to maximize sample analyte ionization and thus increase detector sensitivity.

To make an embodiment of the present invention, such as that shown in FIG. 2, a body material, such as ceramic is provided. The body material is then machined with high precision tools to form the body 34 of the detector 1. The body 34 of the detector 1 is machined to have a detection cavity 3, a column bore 19 and a plurality of bores in which the electrodes 8, 40, 14 and 18 fit. Using ceramics with high precision tooling, the volume of the detector cavity 3 can be created to have a volume as small as approximately 5 $\mu$L. The detector volume can also be very large. However, for applications using a portable or ultrafast GC, a detector volume of approximately 5–100 $\mu$L is desireable and obtainable.

The body surface can then be prepared for bonding to the other components. In one embodiment, the areas 6 of the body 34 that are to be bonded to the other components are metalized using moly-manganese or tungsten-manganese systems. The electrodes 8, 40, 14 and 18 can be bonded to the cup-shaped holders 12 using a method of bonding, such as vacuum brazing. The cup-shaped holders 12, the inlet interface 4, the column interface 5 and the vent interface 20 may then be bonded to the body 34 at the areas that have been metalized. In one embodiment, the components are vacuum brazed to the areas 6 of the body 34 that have been metallized. The proper electrical connections may then be made with the threaded portions 38 of the cup-shaped holders 12. A purge tube 7, which acts as a pathway for the purge gas 24, can be bonded to the column interface 5 and a vent tee 9. The vent tee 9 can be bonded to the vent interface 20, the purge tube 7 and the vent tube 11. The bonding of the electrodes and interfaces to the body 34, in conjunction with the purge gas pathway, create a hermetically sealed discharge ionization detector.

Metallizing of ceramics is a highly technical process. In one embodiment, metallizing involves mixing finely milled powders of molybdenum and molybdenum oxide or tungsten and tungsten oxide with manganese and manganese oxide in a solvent slurry. The slurry can then be brushed or screened onto a clean surface, such as a ceramic body 34, air dried then fired into the surface in a wet hydrogen atmosphere between 1250 and 1700 degrees C. The resulting adherent metallized coating can then be electroless plated or electroplated with nickel and then be available to bond to matching metal parts through vacuum or protective atmosphere brazing using standard brazing alloys. This combination of metallizing and brazing is known in the trade as sintered metal powder seals.

Vacuum brazing is a process well known in the art that creates a bond that is leak tight, non-corrosive, and stronger than alternative joining methods. The first step is positioning together the parts to be joined. Because of tight tolerances, many components fit tightly together and are ready for brazing filler material to be applied to the joining area. The second step is applying the braze alloy to the joining area. Most braze joint areas lend themselves to a slurry of braze alloy powder and a gel binder. The slurry is often applied using needle point tips with foot controlled pneumatic pumps supplying the alloy. Other alloy forms, such as wire, preforms, or foil can be manually applied to the braze area. The final step, vacuum furnace treatment, can be a programmed computerized cycle based on the component material, size or quantity of assemblies, and alloy composition. The vacuum thermal process can include a heat up, preheat, holding period, braze alloy solidification, and quenching steps. Vacuum brazing simultaneously combines bonding, cleaning, and heat treating in one process.

Normally, the brazing of ceramics to metals or to themselves is a difficult matter since standard brazing alloys will not wet ceramics directly. Three options that exist for joining ceramics to metal or to themselves are the aforementioned sintered metal powder seals, active metal brazing, and fused oxide seals.

Active metal brazing involves filler metals containing various percentages of titanium and/or zirconium with other alloying elements. The active metals chemically combine with the oxygen in alumina ceramics or with the carbon or nitrogen in carbides or nitrides to form a bond with themselves or with common metals such as stainless steel, copper, steel, or Kovar. The atmosphere used for active metal brazing is normally a vacuum or inert gas such as helium or argon.

Fused oxide seals are created between two oxide containing ceramic surfaces, such as aluminas, or between oxide ceramics and metals. A suspension of finely ground metallic oxides such as $MnO_2$, $SiO_2$, and $Al_2O_3$ is applied to the seal interface, or preformed washers of this composition are placed between the parts to be sealed, and the assembly is heated in an inert gas atmosphere for a period of approximately 1 to 15 minutes at temperatures ranging from approximately 1200 degrees C to 1500 degrees C. The joined assemblies can then be cooled at a rate rapid enough to prevent complete crystallization or devitrification of the joint. The mix of seal oxides can be modified to match the expansion coefficients of the ceramics or ceramics and metals.

The advantage of the fused oxide seal is that only one firing operation is needed to complete the seal and the seal is rugged both mechanically and thermally.

Although the present invention has been described with reference to preferred embodiments, persons skilled in the art will recognize that changes may be made in form and detail without departing from the spirit and scope of the invention.

What is claimed is:

1. An apparatus for detecting an analyte, the apparatus comprising:
    (a) a detector body having a plurality of electrode bores, a column bore and a detector cavity, the detector cavity having an inlet end and an outlet end;
    (b) an inlet interface sealed to a surface of the detector body at the inlet end of the detector cavity;
    (c) a plurality of electrodes penetrating the detector body through the electrode bores and bonded to the detector body in the electrode bores in a manner that prevents gases from passing past the electrodes;
    (d) a vent tube sealed to the surface of the body at the outlet end of the detector cavity for releasing the discharge gas and any undetected analyte from the detector cavity; and
    (e) a purge gas pathway, having a first end and a second end, wherein the first end extends from the column bore to the second end and the second end is operatively connected to the vent tube,
    (f) whereby the sealing of components and the purge gas pathway prevent air leaks from entering the body, resulting in an apparatus that is hermetically sealed.

2. The apparatus of claim 1, wherein the volume of the detector cavity is in the range of 5–100 micro-liters.

3. The apparatus of claim 1, wherein the detector cavity has a volume of less than 150 micro-liters.

4. The apparatus of claim 1, wherein the body is ceramic.

5. The apparatus of claim 1, wherein the plurality of electrodes comprises:
    (a) a discharge electrode and a second discharge electrode that pass a discharge between them to create ionizing particles;
    (b) a signal electrode that is negatively biased to attract positive ions; and
    (c) a guard electrode that is electrically grounded to eliminate any potential buildup in the detection zone and repel positive ions towards the signal electrode.

6. The apparatus of claim 5, wherein the an end of the discharge electrode projects into the detection cavity to maximize ionization.

7. The apparatus of claim 1, wherein the plurality of electrodes is composed of a refractory metal.

8. The apparatus of claim 7, wherein the refractory metal is molybdenum.

9. The apparatus of claim 1, further comprising a plurality of electrode holders having a first end and a second end, wherein the plurality of electrodes are bonded to the first ends of the electrode holders.

10. The apparatus of claim 9, wherein the electrode holders comprise a threaded portion on the second end for making electrical connections.

11. The apparatus of claim 9, wherein the electrode holders are bonded to the body, wherein the second ends are orientated towards the outside of the detector body, and the plurality of electrodes are bonded to the body by way of the electrode holders.

12. The apparatus of claim 1, wherein the detector body is metallized at points of sealing and bonding.

13. The apparatus of claim 1, wherein the detector cavity is in the form of a conical horn.

14. An apparatus for detecting an analyte, the apparatus comprising:
    (a) a ceramic detector body;
    (b) a cavity formed in the detector body having a volume less than 150 micro-liters, located in the detector body, in which the analyte is detected;
    (c) a discharge system, comprising a second discharge electrode and a first discharge electrode, located in and sealed to the detector body; and
    (d) a signal electrode located in and sealed to the detector body and extending into the cavity for detecting the analyte,
    whereby the sealing of the discharge system and the signal electrode prevents air leaks from entering the body at the interfaces of the discharge system and the signal electrode with the detector body.

15. The apparatus of claim 14, wherein the cavity formed in the detector body has a volume of less than 100 micro-liters.

16. The apparatus of claim 14, wherein the cavity formed in the detector body has a volume of less than 50 micro-liters.

17. The apparatus of claim 14, wherein the cavity formed in the detector body has a volume in the range of 5–100 micro-liters.

18. The apparatus of claim 14, further comprising a guard electrode, located in the detector body and extending into the cavity, the guard electrode being electrically grounded.

19. The apparatus of claim 14, further comprising a vent interface connected to an outside surface of the detector body at an outlet of the cavity, the vent interface being electrically grounded.

20. The apparatus of claim 14, further comprising:
    (a) an inlet interface sealed at an outside surface of the detector body at an inlet end of the cavity, which prevents a gas other than the discharge gas from entering the cavity through the inlet end of the cavity;
    (b) a vent tube for venting a discharge gas and any undetected analyte, the vent tube sealed at the outer surface of the detector body at an outlet end of the cavity;
    (c) a pathway for a purge gas, the pathway having a first end sealed to the outside surface of the detector body around a column bore, and a second end, connected to a vent tube at an outlet end of the cavity, wherein the purge gas prevents a non-analyte gas from entering the cavity through the column bore; and (d) whereby the discharge system and the signal electrode are bonded to the detector body so that no gases may pass through the bonds.

21. The apparatus of claim 14, wherein a tip of the first discharge electrode projects into the cavity.

22. An apparatus for detecting an analyte, the apparatus comprising:

(a) a detector body having a plurality of electrode bores, a column bore and a detector cavity, the detector cavity having an inlet end and an outlet end;

(b) an inlet interface sealed to a surface of the body at the inlet end of the detector cavity;

(c) a plurality of electrodes bonded to the detector body in the electrode bores in a manner that prevents gases from passing past the electrodes;

(d) a vent interface sealed to the surface of the body at the outlet end of the detector cavity and connected to a vent tee;

(e) a column interface sealed to the surface of the body at the column bore; and (f) a purge gas pathway, having a first end and a second end, wherein the first end is connected to the column interface and the second end is connected to the vent tee, (g) whereby the sealing and connecting of components results in an apparatus that prevents air leaks and volatile gases from entering the detector cavity.

23. The apparatus of claim 22, wherein the detector body is ceramic.

24. The apparatus of claim 22, wherein the detector cavity has a volume in the range of 5–100 micro-liters.

25. The apparatus of claim 22, wherein the electrodes are made of a refractory metal.

26. The apparatus of claim 22, wherein, one of the electrodes is a discharge electrode, and wherein a tip of the discharge electrode projects into the detector cavity.

\* \* \* \* \*